United States Patent [19]

Bhatt

[11] Patent Number: 4,999,499

[45] Date of Patent: Mar. 12, 1991

[54] METHOD OF INSPECTING SOLDER JOINTS WITH A LASER INSPECTION SYSTEM

[75] Inventor: Surendra J. Bhatt, Fort Worth, Tex.

[73] Assignee: General Dynamics Corporation, Fort Worth, Tex.

[21] Appl. No.: 411,030

[22] Filed: Sep. 21, 1989

[51] Int. Cl.$^5$ ............................................. G01N 25/72
[52] U.S. Cl. .................................. 250/342; 250/358.1; 374/5
[58] Field of Search ...................... 250/341, 342, 338.1, 250/358.1, 359.1; 374/5

[56] References Cited

U.S. PATENT DOCUMENTS

| | | | |
|---|---|---|---|
| 3,803,413 | 4/1974 | Vanzetti et al. | 250/338.1 |
| 4,657,169 | 4/1987 | Dostoomian et al. | 228/103 |
| 4,696,104 | 9/1987 | Vanzetti et al. | 29/840 |

OTHER PUBLICATIONS

Shea et al., "Certainty of Measurement Using an Automated Infrared Laser Inspection Instrument for PCB Solder Joint Integrity", J. Phys. E: Sci., Instrum., 18, 1985, pp. 677–683.

Streeter, "Solder Joint Inspection Using a Laser Inspector", ASQC Quality Congress Transactions, Anaheim, 1986, pp. 507–515.

Mayben, "Cutting the Cost of Solder Joint Inspection", ASQC Quality Congress Transactions, Dallas, 1988.

Vanzetti, "Automatic Laser Inspection System for Solder Joint Integrity Evaluation", Printed Circuit World Convention III, WCIII-44, 5-84.

Traub, "Overview of Laser/Thermal System Used to Detect Faulty Solder Joints", Electri.Onics, Oct. 1985.

Primary Examiner—Carolyn E. Fields
Attorney, Agent, or Firm—Arthur F. Zobal

[57] ABSTRACT

A method of inspecting solder joints of a circuit card assembly with a laser inspection system having a laser adapted to be operated at a high power in watts to produce a laser beam for a selectable time duration for application to solder joints of a circuit card assembly and a detector system for detecting infra red emission from the heated solder joints to determine the solder joints integrity. For a given type of circuit card assembly and for a given type of solder joint, a laser beam time duration is selected and the laser is operated at a given high power level which is effective to result in the detection of a peak number of defective solder joints of the same type. The time duration of the laser beam employed in the process is that corresponding to the second peak of defective solder joints determined from prior testing.

16 Claims, 13 Drawing Sheets

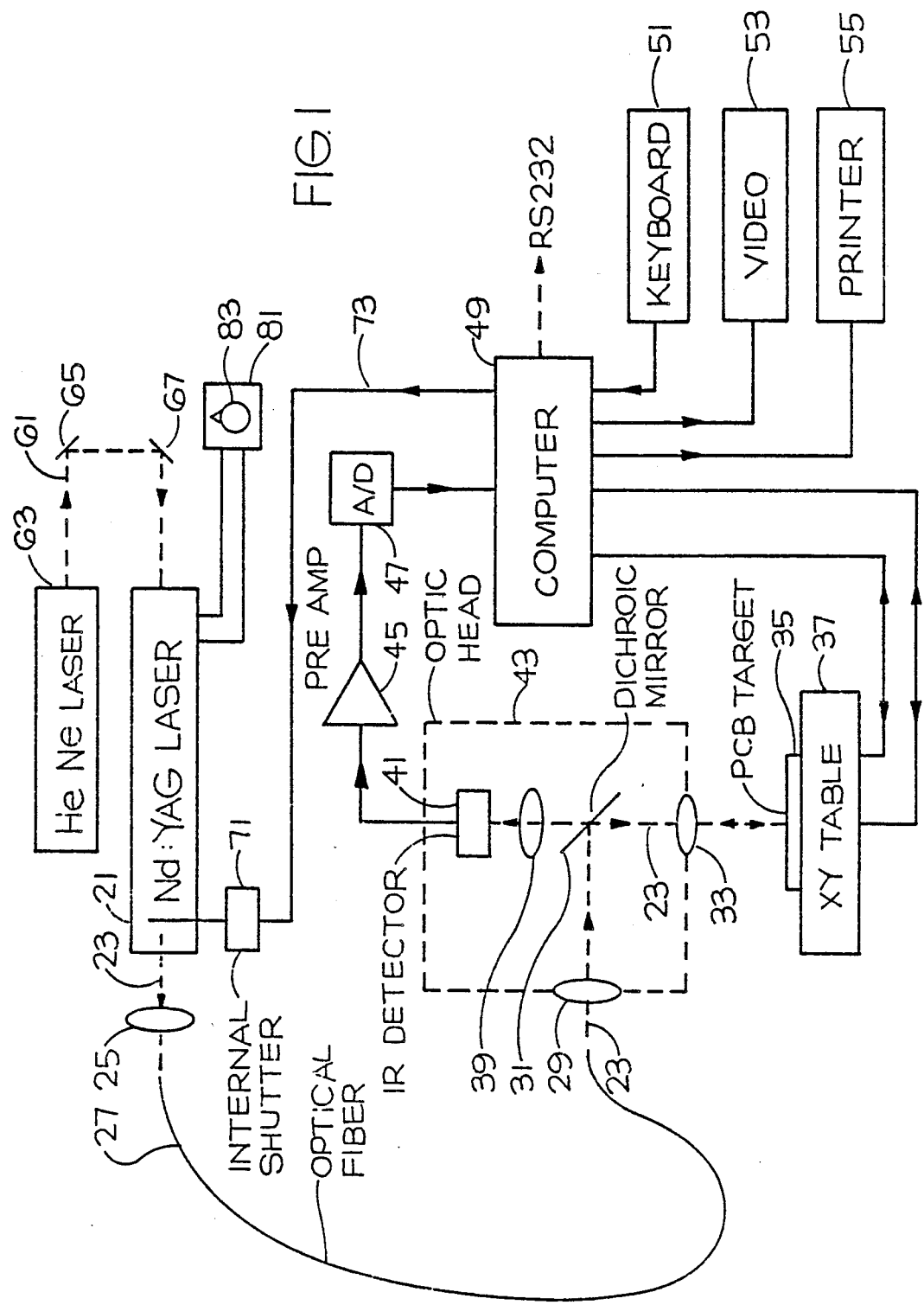

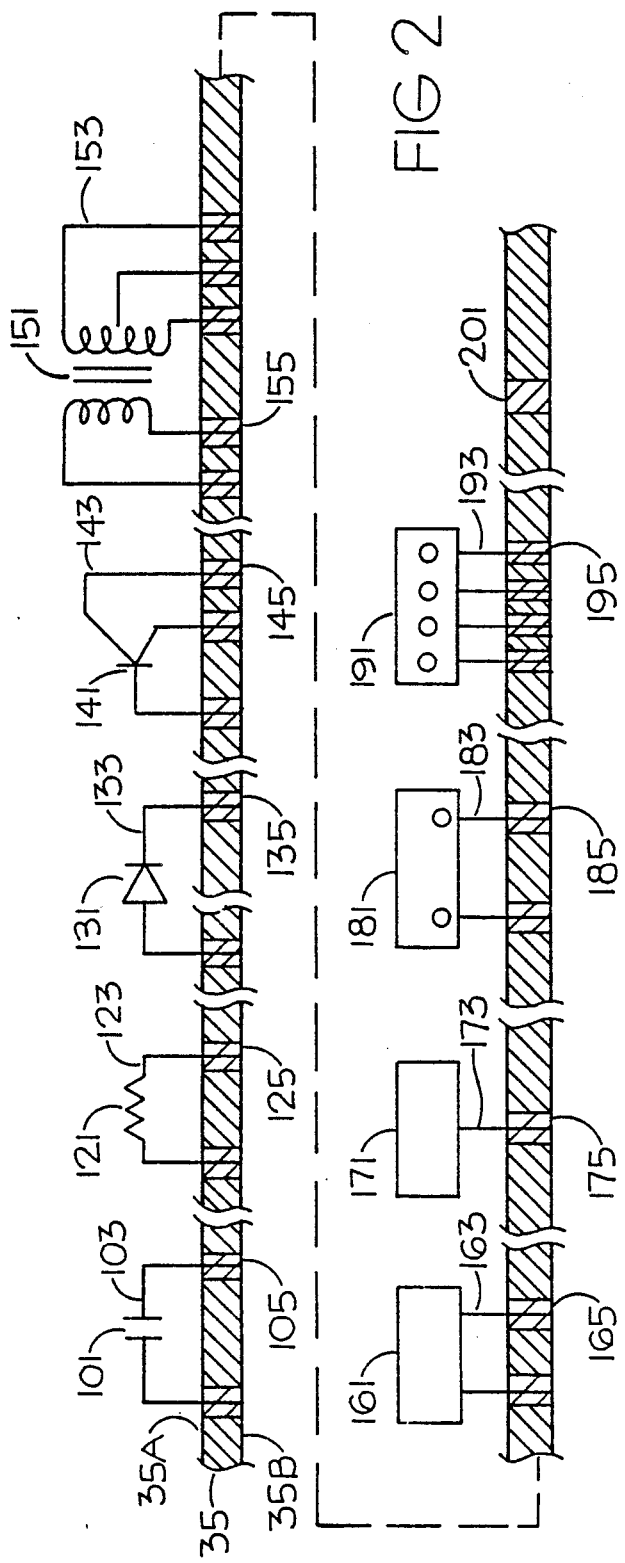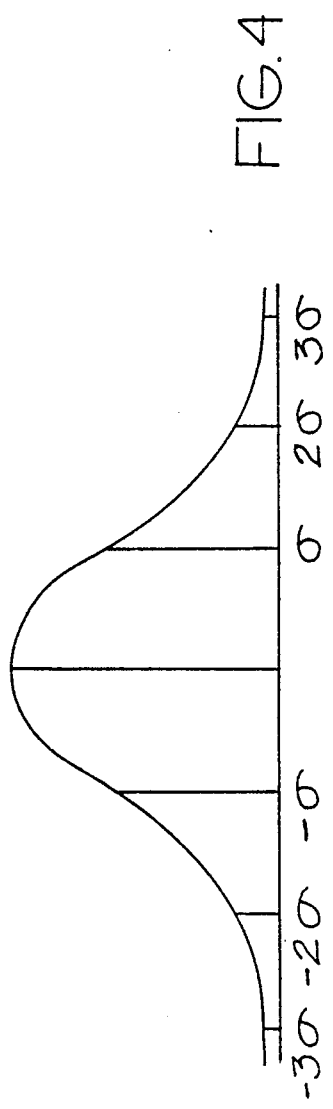

FIG. 5

TABLE OF LASER SETTINGS

| NO. OF LAYERS | CAPACITORS | RESISTORS | DIODES | TO5 CONFIGURATION (TRANSISTORS) | TRANSFORMERS | MICROCIRCUITS DIPS | MICROCIRCUITS SIPS | CONNECTORS 2ROW | CONNECTORS 4ROW | PTHS | LASER POWER (W) |
|---|---|---|---|---|---|---|---|---|---|---|---|
| | | | | | SHUTTER SETTINGS IN MILLISECONDS | | | | | | |
| 3 | 40 | 35 | 35 | 50 | | 50 | 50 | 70 | | 40 | 17 |
| 4 | 50 | 40 | 40 | 50 | | 50 | 50 | 80 | | 50 | 17 |
| 5 | 80 | 80 | 50 | 80 | | 80 | 100 | 100 | | | 17 |
| 6 | 100 | 80 | 70 | 90 | 80 | 90 | 100 | 60 | | 70 | 17 |
| 7 | 100 | 80 | 70 | 100 | | 100 | 100 | 60 | | 60 | 17 |
| 8 | 100 | 80 | 80 | 100 | 80 | 100 | 110 | 80 | | 70 | 17 |
| 10 | 100 | 90 | 100 | 90 | | 100 | 110 | 100 | 120 | 75 | 17 |
| 12 | 70 | 90 | | | | 90 | | 100 | 80 | 80 | 17 |
| 14 | 105 | 100 | 100 | 100 | | 100 | | 100 | 80 | 80 | 17 |

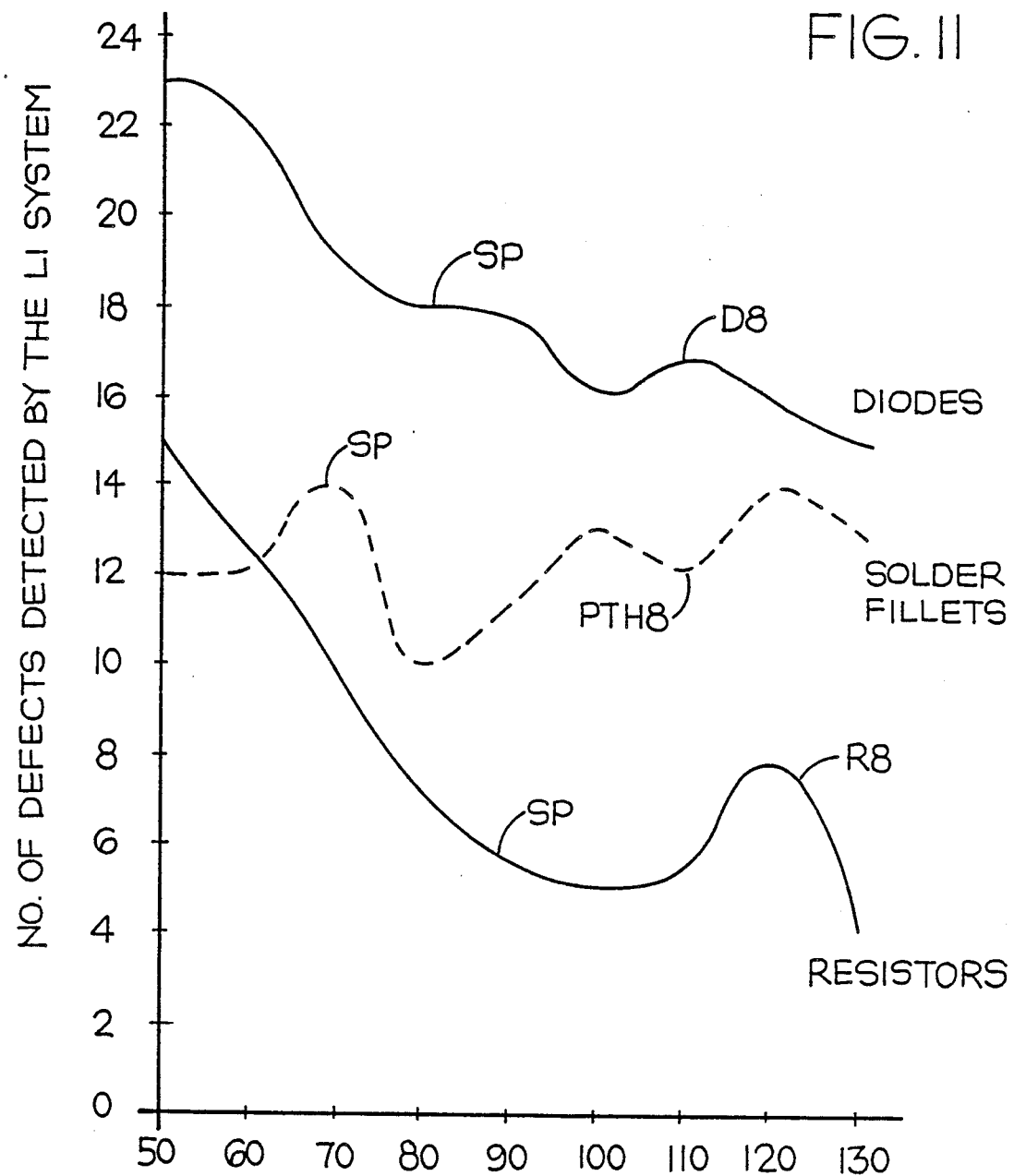

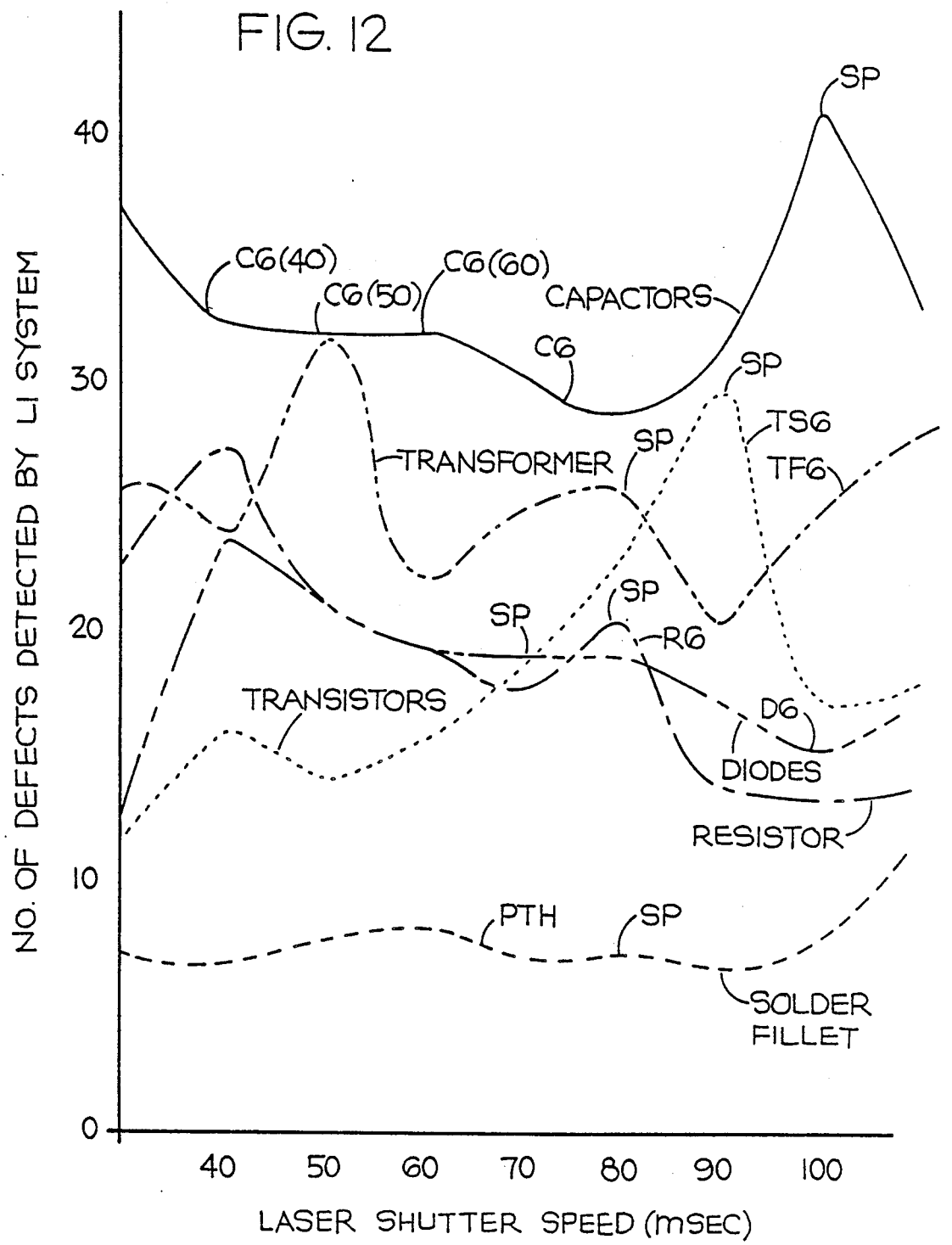

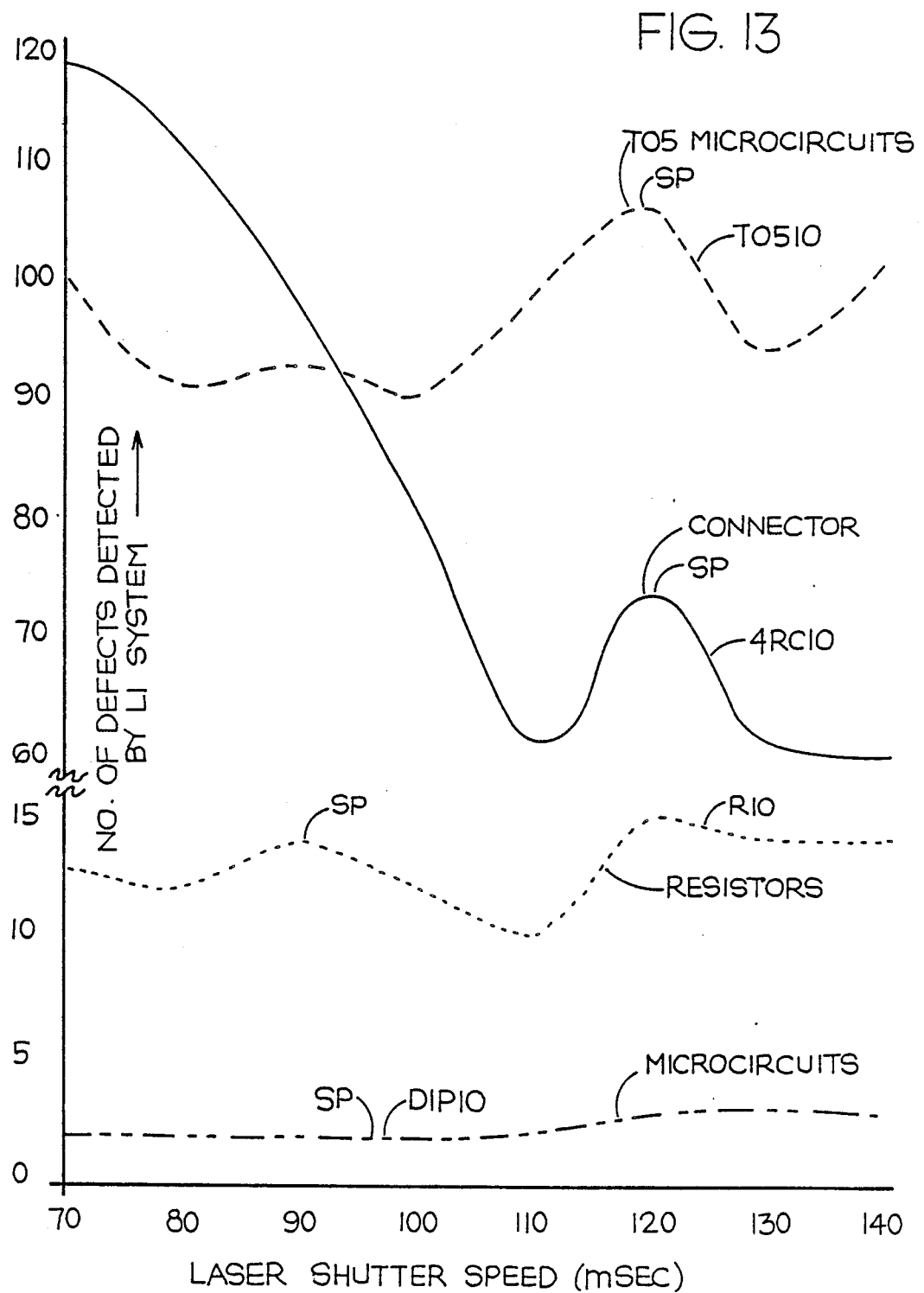

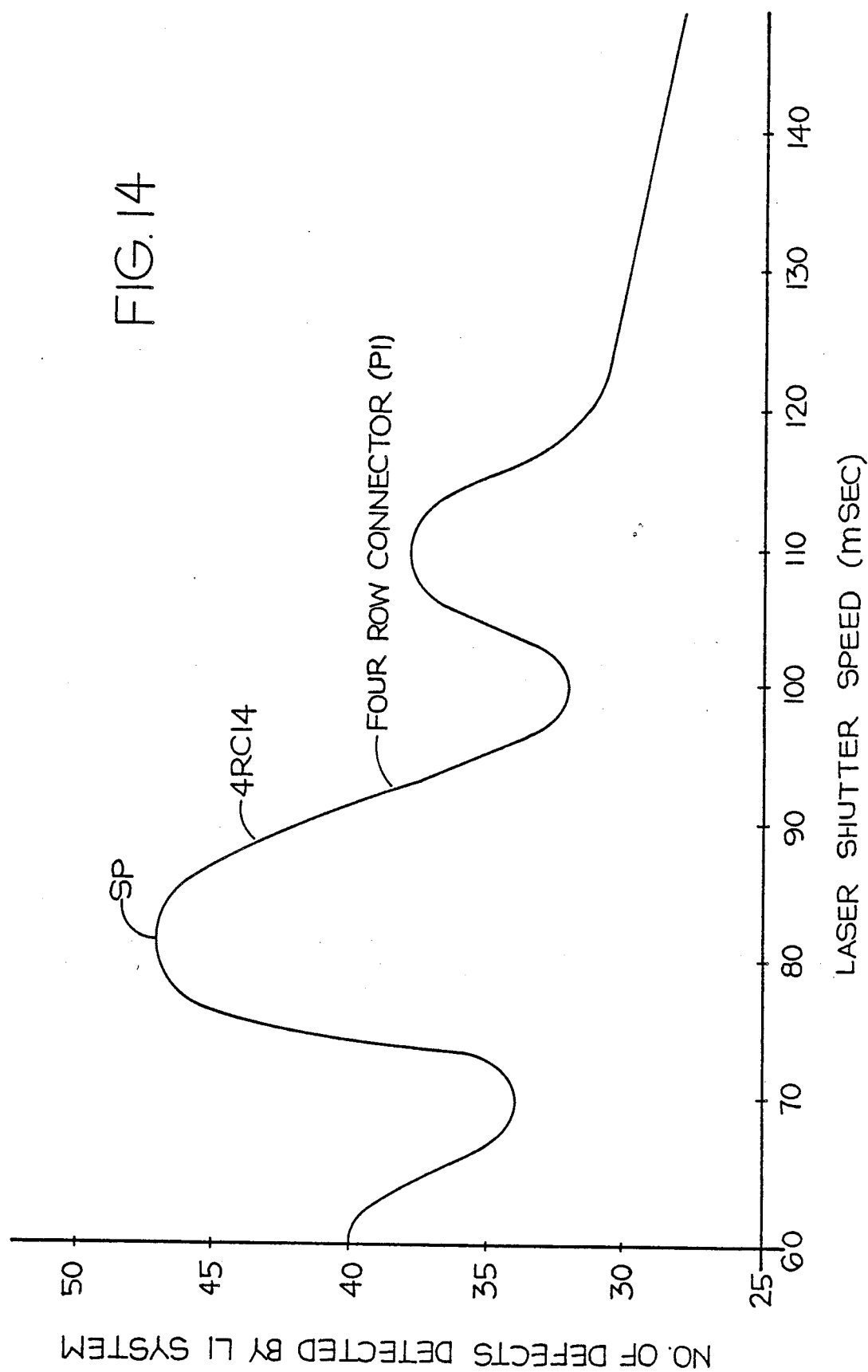

4,999,499

METHOD OF INSPECTING SOLDER JOINTS WITH A LASER INSPECTION SYSTEM

FIELD OF THE INVENTION

The invention relates to the inspection of solder joints in a circuit card assembly using a laser inspection system.

BACKGROUND OF THE INVENTION

In multi-layered circuit card assemblies (also known as printed wiring assemblies or circuit board assemblies), component leads are connected to the layers by forming holes through the card assembly at selected positions; locating the leads in the holes; and soldering each of the leads to all of the layer portions surrounding the holes. Circuits extend to selected layer portions to form the complete circuit card assembly.

It is important to determine whether the solder joints are defective or good. It is known to inspect solder joints with a laser inspection system including a laser and a detector. The laser is operated to apply a laser beam to the solder joint to heat the joint for a given time and the laser beam is switched off with a shutter mechanism. The hot solder joint emits infra red emission which is measured to determine the cooling properties of the joint. The cooling rate determines the condition of the solder joint as to whether the solder joint is defective or good. This process is disclosed in U.S. Pat. Nos. 4,696,104; 4,657,169; and 3,803,413. Reference also is made to 1986-*ASOC Quality congress transaction—Anaheim,* "Solder Joint Inspection Using a 'Laser' Inspector", J. P. Streeter, pp 507–515; *Printed Circuit World Convention III*, May, 1984, "Automatic Laser Inspection System for Solder Joint Integrity Evaluation", Dr. Riccardo Vanzetti; and Electrionics, October 1985, "Overview of Laser/Thermal system Used to Detect Faulty Solder Joints", Alan C. Traub. Heretofore, the method of deciding correct shutter speed (In this application shutter speed is defined as the time duration which the laser beam is fired on the solder joint) has been based on microsectioning the solder joints and determining the correct shutter speed on classification of defects found during microsectioning. For example, large voids in solder joints are considered as a higher level of defect whereas small voids are considered as a lower level of defect. The major disadvantage of this method of inspection is that the laser shutter speed cannot be set without data obtained from microsectioning first (a destructive method).

At lower laser power, a solder joint is heated uniformly together with the lead yielding a false determination of the condition (defective or good) of a solder joint.

SUMMARY OF THE INVENTION

It is an object of the invention to provide a new and enhanced laser inspection process for inspecting solder joints of a circuit card assembly without the need of microsectioning solder joints.

In carrying out the inspection process, a laser is employed to apply a laser beam to the solder joint to be inspected and a detector system is employed to detect infra red emission from the heated solder joint to determine the integrity of the solder joint. For a given type of combination of circuit card assembly and components, a laser beam time duration is selected and the laser is operated at a given power level which is effective to result in the detection of a peak number of defective solder joints of the same type. The laser is operated at said given power level to apply a laser beam to the solder joint to be inspected for said selected time duration, for heating the solder joint. Infra red emission from the heated solder joint is detected to determine the integrity of said solder joint.

In the preferred embodiment, the time duration of the laser beam employed in the process is that corresponding to the second peak of defective solder joints of the same type determined from prior testing.

In addition, in the preferred embodiment, in carrying out the process, the laser is operated at a high power level in watts.

It is an object of the invention to produce a function which reflects the second peak of defective solder joints.

BRIEF DESCRIPTION OF THE DRAWINGS

FIG. 1 is a block diagram of the system employed for carrying out the process of the invention.

FIG. 2 is a cross-sectional view of a circuit card assembly with solder joints to be inspected.

FIG. 4 is a normal distribution of infra red emissions detected (measured in P units) of occurrences of good solder joints and which indicates the average and variance, with sigma limits indicated on each side of the average.

FIG. 5 is a table of laser shutter settings.

FIGS. 6–14 are plots of the number of defective solder joints detected by a laser inspection system against the laser shutter speed at high laser power for the solder joints of the different types of circuit card assembly components listed in the table of FIG. 5 FIGS. 6–14 have one or more curves or plots. Some of the curves of FIG. 6–14 were obtained from the inspection of solder joints of the same type of circuit components but installed in circuit card assemblies having a different number of layers.

DESCRIPTION OF THE PREFERRED EMBODIMENTS

Figure 3:
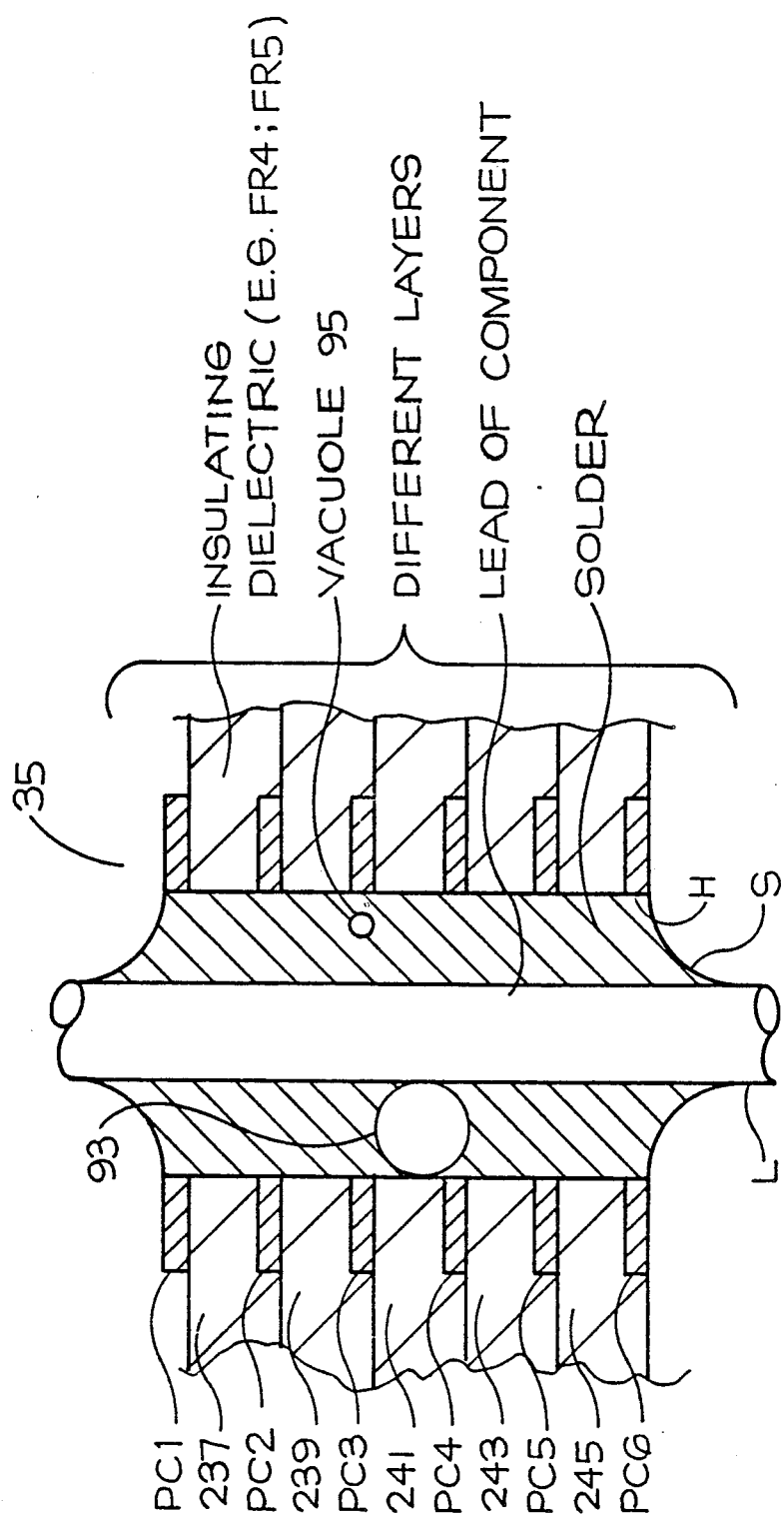
FIG. 3 is an enlarged partial cross-sectional view of a multi-layered circuit card assembly with a solder joint.

Referring now to FIG. 1, the laser inspection system comprises a Nd: YAG laser 21 whose output beam 23 is focused by a lens 25 into an optical fiber 27 where it emerges from the other end with a given divergence angle. It is then incident upon a focusing lens 29 from which it proceeds to a dichroic mirror 31 which reflects the beam downwardly upon a focusing lens 33. The function of the lens 33 is to focus the laser beam upon the solder joint of a circuit card assembly (CCA) 35 which in turn is mounted on an XY table 37. The lens 33 directs upwardly some of the thermal radiation which leaves the heated target (solder joint). This radiation is at greater wave length than the YAG radiation, being typically in the range from about 2.5 to 5.5 micrometers. The dichroic mirror 31 is specifically designed so as to be largely transparent to the longer wave length region so that most of the thermal radiation passes through it to another lens 39 which focuses the thermal radiation upon an infrared detector 41. Lens 33, mirror 31, lens 39, and infrared detector 41 are supported in an optic head 43. The infrared detector signal is preamplified at 45 and is digitized by an analogue-to-digital(A/D) converter 47, the output of which is applied to a computer 49 of the type identified as a DIGITAL SMS computer produced by Digital Equipment Corporation. The computer 49 has a keyboard 51, a video display 53, and a printer 55 coupled thereto.

A helium neon (HeNe) laser beam 61 from a HeNe laser 63 is passed through the center of the cavity of the YAG laser such that the HeNe beam follows the same path as that of the YAG. This is helpful during manual solder joint programming operations when the various solder joint locations are being entered into the computer 49 since power of the HeNe is very low and its beam is visible. This is done by means of a table-control means which moves the table 37 so that each solder joint in turn is located at the HeNe beam, whereupon its location is automatically entered into the computer when the operator presses the appropriate key.

Member 71 is an internal shutter which is controllable by the computer 49. The time duration of the laser beam 23 can be varied from about 1 milliseconds to about 1 minute or longer.

Power is supplied to the YAG laser 21 by way of an AC power supply 81. The electrical power in watts to operate the YAG laser 21 can be controlled by a knob 83 located on AC power supply. The YAG laser 21 can be operated in electrical power in watts from about 5 to 23 watts.

The laser inspection system of FIG. 1 is commercially available from Vanzetti Systems, Inc. of Stoughton, Mass. and is fully disclosed in U.S. Pat. Nos. 4,696,104, 4,657,169, and 3,803,413 which are incorporated into this application by reference.

Referring now to FIG. 2, there is illustrated schematically in cross-section a printed circuit card assembly (CCA) 35 which may include a number of component such as capacitors 101, resistors 121, diodes 131, transistors 141, transformers 151, microcircuits such as DIPS (Dual-In-Line Packages) 161 and SIPS (Single-In-Line Packages) 171, two-row connectors 181, and/or four-row connectors 191, all of which are located on the component side 35A of the card and have their leads located in holes in the card and soldered to the layers of the board. Reference number 201 identifies a PTH, also known as a plated through hole comprising a hole filled only with solder. The various layers of the card 35 are not shown in FIG. 2.

The capacitor 101, resistor 121, and diode 131 each will have two leads of type 103, 123, and 133 located and soldered in holes 105, 125, and 135 respectively and the transistor 141 and transformer 151 each will have more than two leads of type 143 and 153, located and soldered in holes 145 and 155 respectively. Although the DIPS 161, SIPS 171, two-hole connectors 181 and four-hole connectors 191 are shown with only one or two leads such as 163, 173, 183, and 193, located and soldered in holes 165, 175, 185, and 195 respectively, in actuality, the microcircuit packages like DIPS 161 can have six to one hundred and forty leads located and soldered in a corresponding number of holes; the SIPS 171 can have about eight leads located and soldered in eight holes respectively; and the two-row and four-row connectors 181 and 191 each can have sixteen to one hundred and twenty eight leads, located and soldered in a corresponding number of holes respectively. The PTHS 201 are provided to allow electrical connection between various layers of a CCA. A given type of CCA will have all or a combination of the components 101, 121, 131, 141, 151, 161, 171, 181, 191, and 201 and possibly other types of components. The number of each of these components for a given type of CCA will vary.

Most CCAs will have more than two layers, for example, 3, 4, 5, 6, 7, 8, 10, 12, or 14 layers. The CCAs for defense purposes have mostly 6, 7, or 8 layers.

A portion of a six layer CCA 35 is shown in FIG. 3. The card of FIG. 3 is formed from five basic layers of resin 237, 239, 241, 243, and 245 with printed circuits PC1 and PC6 formed on the outside of layers 237 and 245; printed circuit PC2 located between resin layers 237 and 239; printed circuit PC3 located between resin layers 239 and 241; printed circuit PC4 located between resin layers 241 and 243; and printed circuit PC5 located between resin layers 243 and 245. The printed circuits PC1-PC6 define the six layer circuit card and are formed of suitable electrically conductive material. The resin layers may be formed of an electrical insulating material, e.g. FR4 or FR5 resin. Generally the printed circuits PC1-PC6 are formed of copper. A hole H extends through the card 35 and PC layers PC1-PC6 will surround the hole H and depending on the component lead L to be inserted into the hole H and soldered to the PC layers PC1-PC6, at least one of the layers PC1-PC6 will extend from the hole H to other components of the circuit card while the other layers may have no connections from the PC portions surrounding the hole H to the other components of the circuit card. Thus, in this case, although the lead L will be soldered to all of the PC layer portions surrounding the hole, the lead L may be electrically connected to at least one other circuit card component. The solder in the hole L is identified as S and usually consists of Sn/Pb(60/40) which is 60% tin and 40% lead. The lead L may be of copper or an alloy known as KOVAR. The solder S for a good solder joint will contact all of the PC layer portions surrounding the hole H and the lead L located in the hole H. In the case of the PTH 201, the hole H will be filled with solder S. Circuit card having 3, 4, 5, 7, 8, 10, 12, and 14 layers and their soldered joints will be formed in a manner similar to that described with reference to FIG. 3, however, the 3, 4, and 5 layer card will have 3, 4, and 5 PC layers respectively and the 7, 8, 10, 12, and 14 layer card will have 7, 8, 10, 12 and 14 PC layers respectively with the solder S joined to different PC layers, and to the component lead inserted therein in the case of solder joints for components 101, 121, 131, 141, 151, 161, 171, 181, and 191.

In order to inspect the solder joints of the CCA 35, or other circuit cards, the CCA is placed on the table 37 with its solder side 35B facing upward. The laser system is operated at high power and the laser beam 23 is applied to each solder joint at a shutter speed dependent upon the function of the solder joint, i.e whether it connects the lead of a capacitor, resistor etc. to the PC layers of the circuit card or whether it is a PTH.

When the system of FIG. 1 was purchased from Vanzetti Systems, Inc., I was informed by the representatives of Vanzetti Systems, Inc., not to operate the laser system at more that 12 watts and not to operate the laser at a shutter speed of greater that 30 milliseconds or the solder joint to be inspected would melt. I have found, however, that at lower laser power, a solder joint is heated uniformly together with the lead inside the solder joint yielding false determination of the acceptance or rejection of a solder joint. However, if the laser power is set high (15 watts or more), it will tend to heat the solder joint faster than a lead of a component and readings can be taken before the lead inside the solder joint can affect the heat transfer within the circuit card assembly or external to the environment, thereby avoiding the problems associated with inspection at low laser power.

After selecting a high laser power (17 watts), I determined the best shutter speed for inspecting solder joints in the following manner. I selected ten circuit card assemblies (CCAS) each having six layers and consisting of different types of components (e.g. capacitors, resistors, DIP, SIP), etc.

I inspected the solder joints of these CCAs with the laser inspection system (LI system) of FIG. 1. I recorded the rejects of the LI system for different shutter speeds of the laser for solder joints of different components or function (capacitors, resistors, DIP, SIP, etc.). The system as purchased has it own program for inspecting solder joints. In the process recommended by the manufacturer, the laser is operated at 12 waats and the shutter speed used is 30 milliseconds. The profile of the board is entered into the computer program. The profile consists of a number assigned to the board, the number of joints to be inspected and their XY locations, designation of the components of the leads to be inspected, a tilt or straight position for the head, and the shutter speed, which according the normal operation of the system is 30 milliseconds. I varied the normal operation of the system in that I inspected each joint at a different number of shutter speeds. I also operated the laser at 17 watts. In determining the condition of the joints, the system measures the cooling rate of the joint after irradiation of the joint by the laser beam. The cooling rate of good joints will exhibit a normal (bell shaped) distribution. Referring to FIG. 4, for the average of cooling rates of good solder joints, shown as the peak, in the band of plus and minus sigma, 67% of the good solder joints will be found; in the band of plus and minus two sigma, 95% of the good solder joints will be found; and in the band of plus and minus three sigma, 99% of the good solder joints will be found. I used the three sigma band. I instructed the computer, in accordance with its program to print out the rejects.

A software, supplied by Vanzetti systems of Stoughton, allows a user of the Laser Inspection System (LI System) to obtain four different points of the cooling curve of a solder joint. The cooling curve is defined as the amount of IR radiation detected from a heated solder joint as a function of time. The four points are Peak Thermal Unit (P-unit); Middle Thermal Unit (M-Unit); Lower Thermal Unit (L-unit) and Final Thermal Unit (F-Unit) These are digital units, representative of IR radiation detected, taken at an interval of 5 milliseconds apart, with the P-unit beginning at 3 milliseconds after the laser beam is terminated. The division between "in limit" and "out of limit" of solder joints is based upon statistical calculations of P-units of different identical solder joints.

Let us consider a solder joint "A" for a type of Circuit Card Assembly (CCA) P-units of "A" for CCA #1;#2;#3; . . . . . #n for a given shutter speed; are collected. These P-units will exhibit normal distribution. Therefore the following calculations will be applicable:

$$P_m = \{P_1 + P_2 + \ldots + P_n\}/n \qquad 1$$

where 1;2;3; . . . n are number of CCAs of same type. $P_n$ is P-unit of solder joint "A" of $n^{th}$ CCA. $P_m$ is mean of P-units for solder joint "A".

Standard Deviation (also known as sigma) of solder joint "A" can be calculated as follows:

$$S.D._A = \sqrt{\frac{\{(P_m - P_1)^2 + (P_m - P_2)^2 + \ldots + (P_m - P_n)^2\}}{(n-1)}} \qquad 2$$

where $S.D._A$ is standard deviation of solder joint "A" and n is the total number of CCA in a sample.

While one can calculate these parameters by laborious manual method, Vanzetti systems, software does just the same. Hence the direct "in limit" and "out of limit" solder joints can be identified much more quickly.

The following is an example of how a three sigma limit works for a given shutter speed:

| | |
|---|---|
| Standard deviation of solder joint "B" | = 15 P-units. |
| Average of solder joint "B" for 10 CCAs | = 150 P-units. |
| Therefore upper limit − three sigma | = 195 P-units. |
| Also lower limit − three sigma | = 105 P-units. |

The above example suggests that all solder joints "B" that will be inspected by the LI System will either be classified as "in limit" or "out of limit" depending whether their P-units are within 105 and 195 or not. All the solder joints "B" which do not have P-units within 105 and 195 shall be identified on a print out.

As a specific example, assume solder joint "B" is a capacitor joint. For the ten, six layer CCAs I inspected all of the capacitor solder joints with the LI System at a plurality of shutter speeds. Referring to FIG. 12, to obtain curve C6, I inspected all of the capacitor solder joints of the ten CCAs at 40 mSec shutter speed and instructed the computer to print out all rejects. I added all of these rejects and obtained point C6(40). I carried out the same procedure at shutter speeds of 50 mSec, 60 mSec, etc., to obtain points C6(50) C6(60),etc. I then plotted the number of laser rejects against shutter speeds for the capacitor solder joints to obtain curve C6. I carried out the same procedure for other types of solder joints in the ten, six layer CCAs to obtain curves TS6, TF6, R6, D6, and PTH of FIG. 12. The solder joint curves of FIGS. 6–11, 13 and 14 were obtained using the same procedure on CCAs having different numbers of layers which are explained in more detail subsequently.

Thus, all such solder joints of groups of components (e.g. capacitors; resistors; diodes; DIPs; etc) for a sample of CCA representing a set number of layers and for a given shutter speed are collected. Such "out of limit" solder joints for different shutter speeds for the same given number of layer are collected and plotted. See FIGS. 6 to 14.

For the inspection process of my invention, I selected the shutter speed setting based on the Second Peak of rejects found in the plots and programmed these settings in the profile for the circuit card assembly The Second Peak of rejects in the plots give a shutter speed which I believe to be the best shutter speed for inspecting a solder joint of a given component or function of a circuit card assembly having a given number of PC layers. I call this the Second Peak theory.

Using the profile, I verified the Second Peak theory as follows. I selected a production CCA at random and inspected solder joints of this circuit card assembly with the LI system operated at 17 watts and using the appropriate shutter speeds found at the second peaks of rejects plotted against shutter speeds. The LI system identified different laser rejects (out of the ±3 sigma limits) and laser accepts (within the ±3 sigma limits). More than 30% of these solder joints were selected at random and microsectioned. Statistically, it was found, that the laser accepts were good solder joints and that solder joints with a 10 mil void at a depth of 75% or less from the solder side were identified as defective joints by the LI System.

A bad or defective solder joint is defined as a solder joint having internal voids of 10 mil in size or larger and within 75% of the thickness of the solder joint from the solder side. The diameters of the holes in the circuit card generally are 30 mils. The diameters of the leads generally are 10 mils. A void having a dimension of 10 mils generally will bridge the wall of the hole and the lead. Such a void is shown at 93 in FIG. 3 and results in a bad joint. Voids having dimensions of 8 or 9 mils also are undesirable. Small voids known as vacuoles which do not contact the sides of the hole of the lead do not significantly affect the joint integrity. A vacuole is shown at 95 in FIG. 3.

I repeated the above process of verifying laser inspection results of solder joints using shutter speeds at the Second Peak through microsectional verification on seven different types of CCAs. These CCAs varied from three layers to fourteen layers in construction For each circuit card assembly, shutter speeds at the Second Peaks were verified to give accurate results for solder joints of different component types, or functions.

FIG. 5 is a table of laser shutter speeds which give the best inspection results and which were found at the second peak for the solder joints indicated; for the circuit card assemblies having the indicated number of PC layers; and for the laser operated at 17 watts.

In the table of FIG. 5, the first column indicates the number of PC layers of the circuit card assembly; columns two through eleven give the shutter speed or setting found at the second peak for the solder joints of the components or types indicated; and column 12 indicates the power in watts at which the laser was operated.

As can be seen from the table of FIG. 5, for a solder joint of a given component, the shutter settings at the second peak generally increases as the layers of the circuit card increase, particularly from a three layer circuit card to a six layer card, although this is not true in all cases. Moreover, the shutter speed at the second peak generally is different for solder joints of different components or types in circuit cards having the same number of layers. Some of the actual plots of the number of solder joint rejects against laser shutter speeds for solder joints of the various components or types as shown in the table of FIG. 5 are shown in FIG. 6–14. As can be seen, some of these plots have three peaks. On the six layer boards that I originally tested I could not find many of the defective joints using the shutter speed at the first peaks. It is believed that this is due to reduced energy of the laser beam. I reset the shutter speeds indicated for the second peaks and was able to detect the defective joints having 8, 9, 10 mil voids. If I used shutter speeds at the third peaks I would have also detected the less than 8 mil voids (vacuoles) which do not seriously affect the joints, integrity. Other detrimental effects are present in using shutter speeds at the third peaks in that the joints may be heated too much thereby creating other problems.

Figure 6:
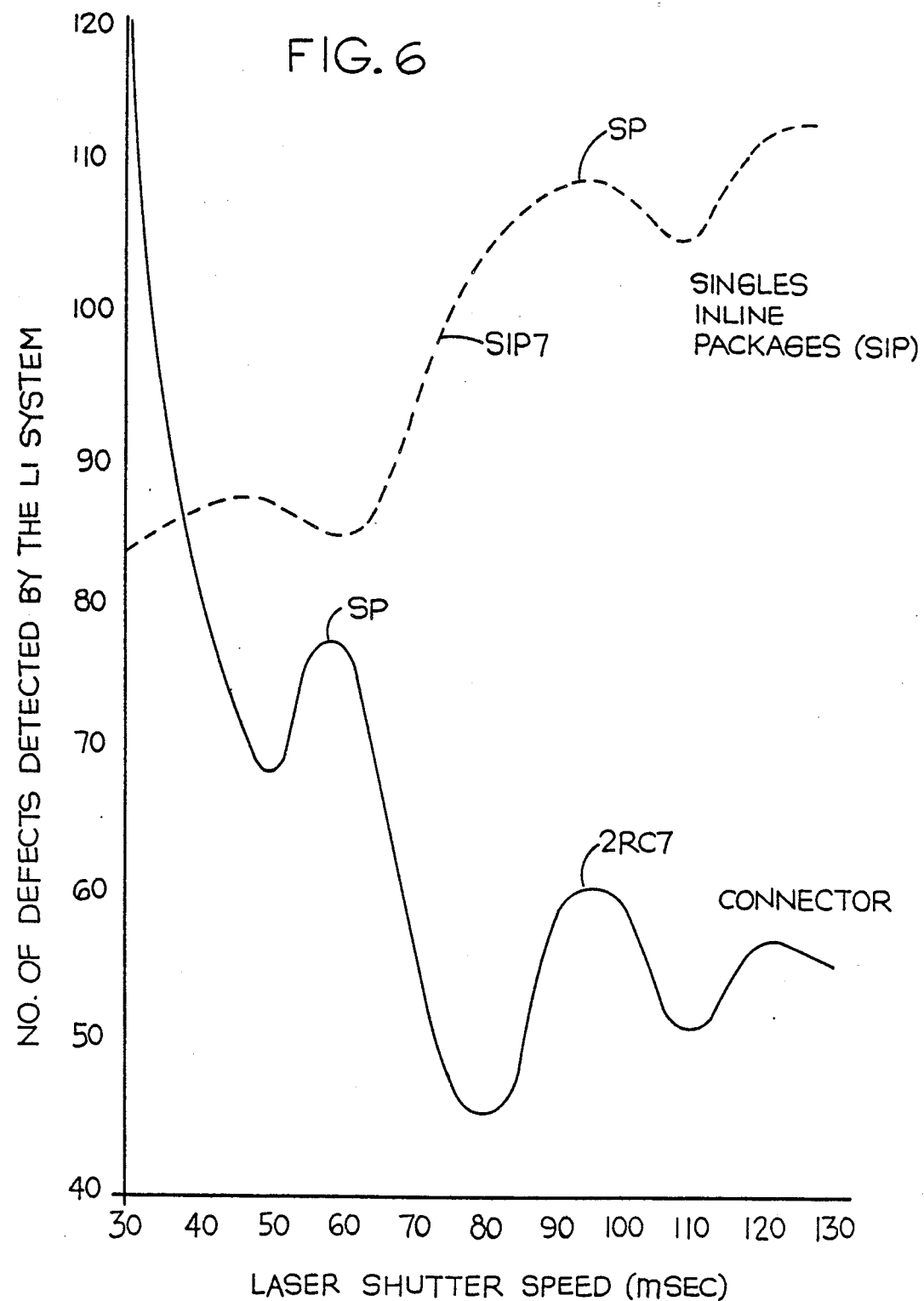
Figure 7:
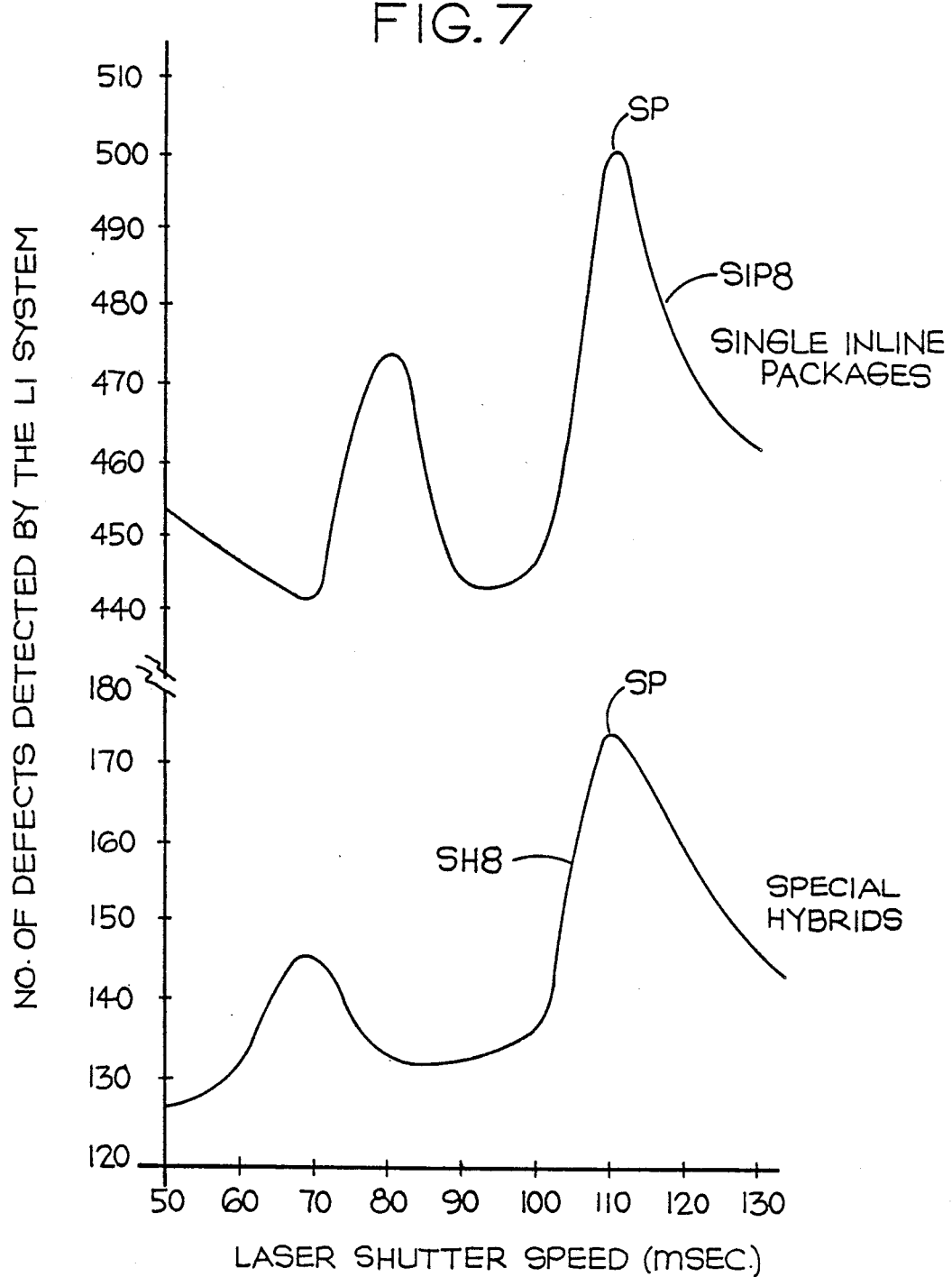

The curves SIP7 and 2RC7 of FIG. 6 were obtained from solder joints of a SIP and a two row connector respectively in seven layer circuit cards. The curves SIP8 and SHP8 of FIG. 7 were obtained from solder joints of a SIP and a special hybrid microcircuit similar to that of a DIP respectively in eight layer circuit cards. The curves DIP8 and TR12 of FIG. 8 were obtained from solder joints of a DIP and a transformer in twelve layer circuit cards. The curves T058 and DIP8 of FIG. 9 were obtained from solder joints of a special transistor circuit and a DIP respectively in eight layer circuit cards. The curves 2RC8 and C8 of FIG. 10 were obtained from solder joints of a two row connector and a capacitor respectively in eight layer circuit cards. The curves D8 and R8 of FIG. 11 were obtained from solder joints of a diode and a resistor respectively in eight layer circuit cards and the curve PTH8 of FIG. 11 was obtained of a PTH of eight layer circuit cards In FIG. 12, all of the curves were obtained from solder joints in six layer circuit cards. Curve C6 was obtained from capacitor joints; curve TS6 was obtained from a transistor joints; curve TF6 was obtained from transformer joints; curve R6 was obtained from resistor joints; curve D6 was obtained from diode joints; and curve PTH was obtained from PTH joints.

The curves T0510, 4RC10, R10 and DIP10 of FIG. 13 were obtained from solder joints of a special transistor circuit, a four-row connector and resistors, in ten layer circuit cards. The curve 4RC14 of FIG. 14 was obtained from solder joints of a four row connector in fourteen layer circuit cards.

Figure 8:
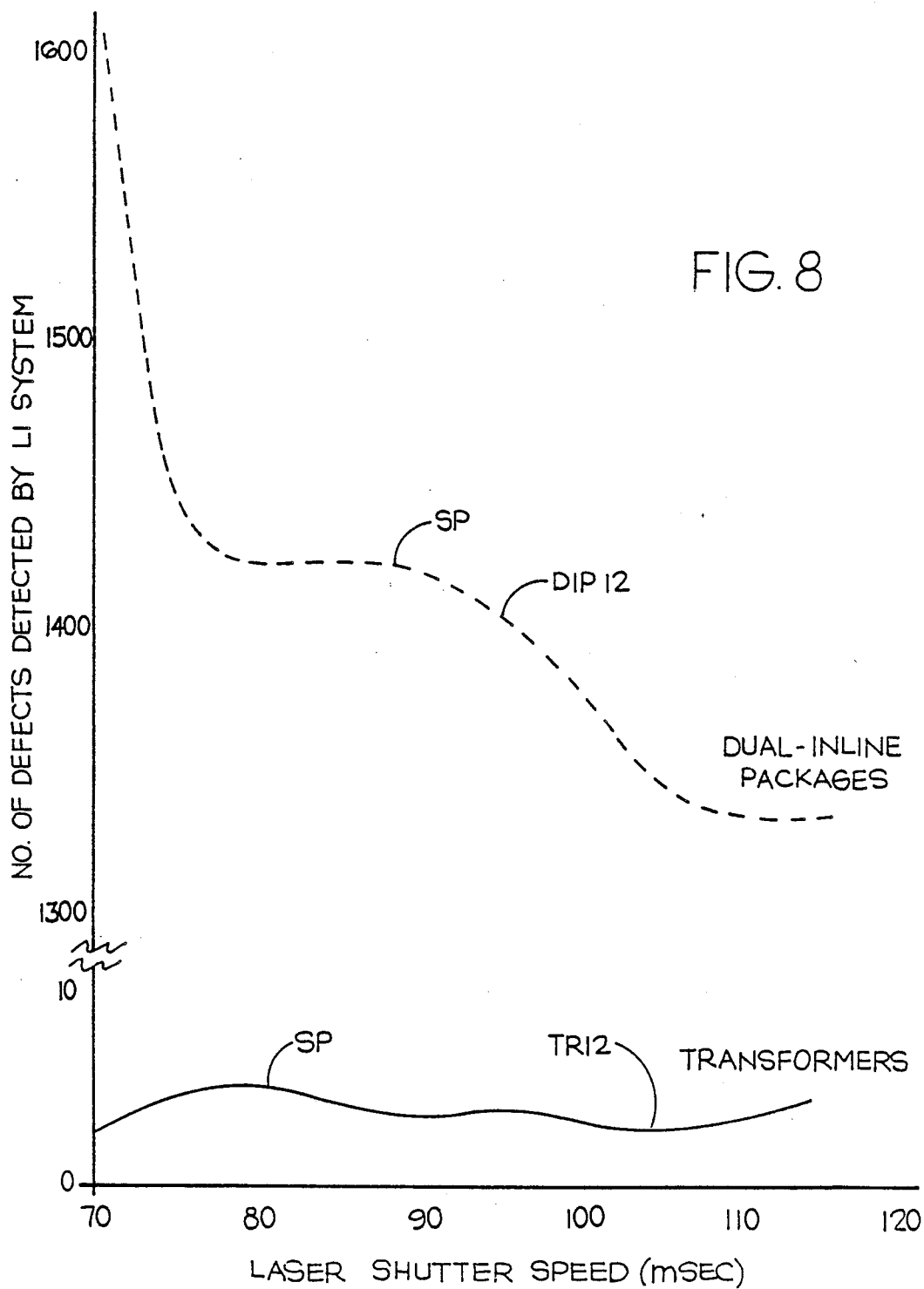
Figure 9:
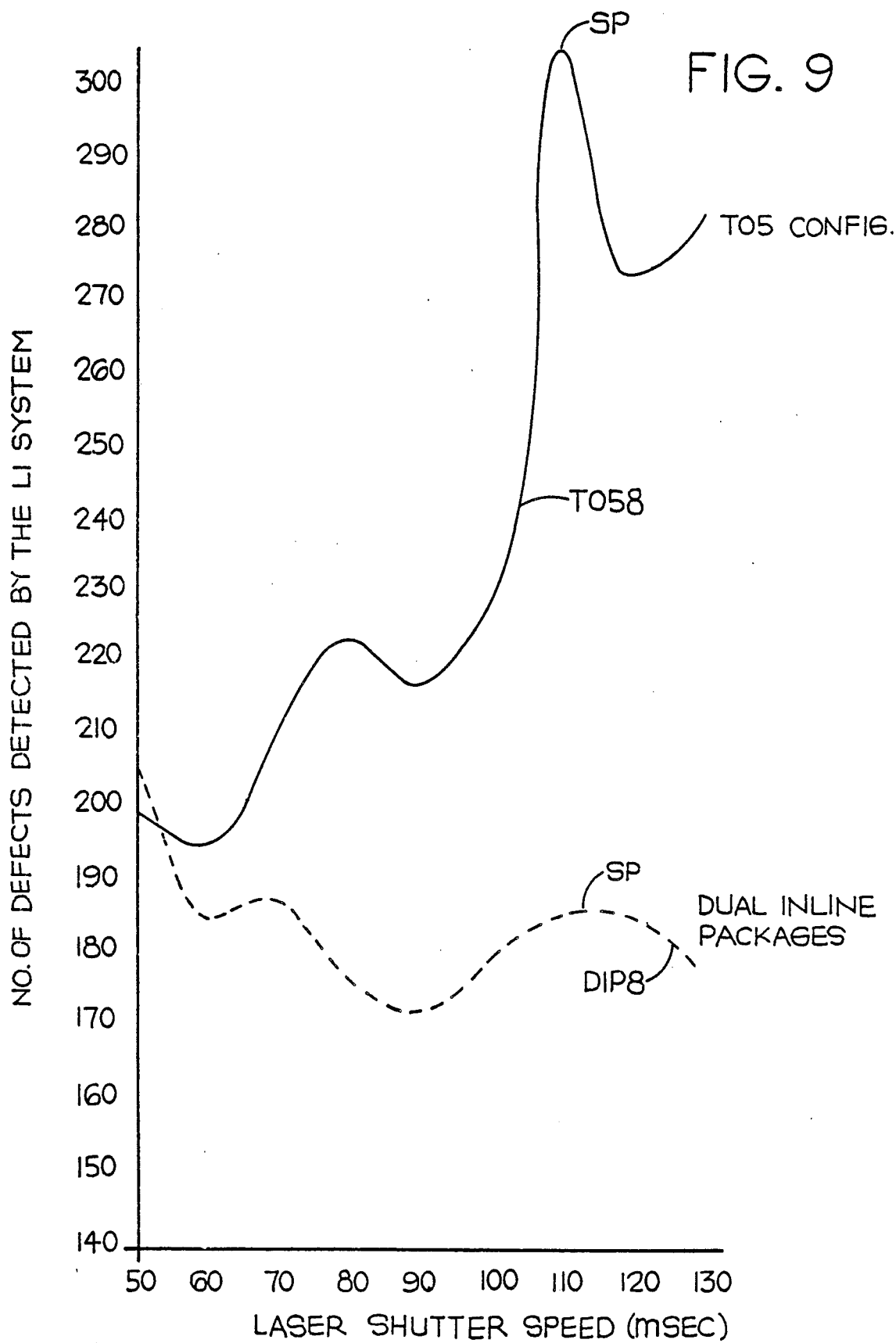
Figure 10:
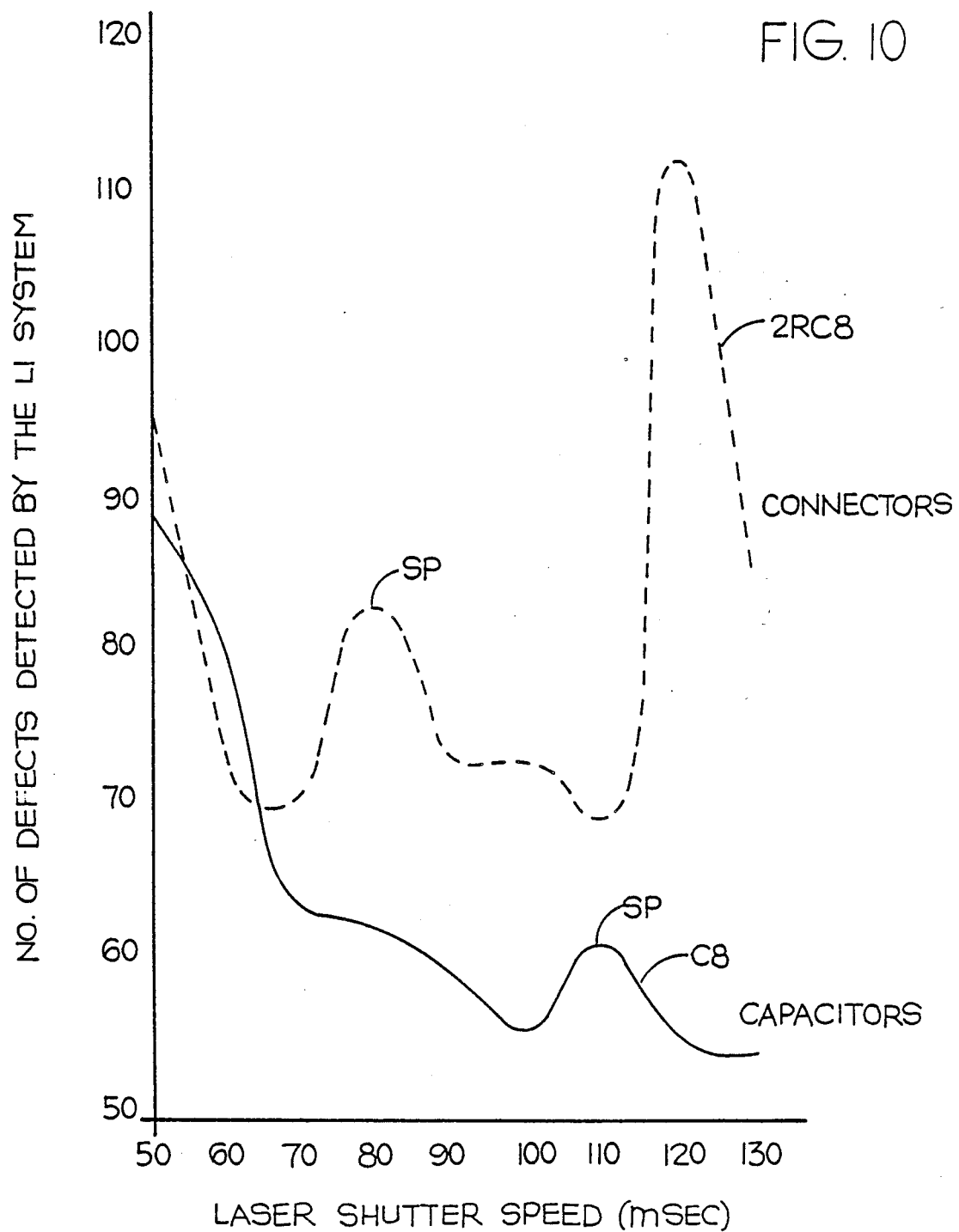

In FIGS. 6–14, the second peaks of the curves are indicated by SP. In the curve 2RC7 of FIG. 6, the first peak is below 30 milliseconds. In FIG. 8, the first peaks of the curves DIP12 and TF12 are below 70 milliseconds. In FIG. 10, the first peaks of the curves 2RC8 and C8 are below 50 milliseconds. In FIG. 11, the first peaks of curves D8, PTH8 and R8 are below 50 milliseconds. The second peak of curve D8 is estimated to be on the plateau shown and the second peak of curve R8 is not clearly shown In FIG. 12, the first peak of curve C6 is at the plateau to the left of the second peak. In FIG. 12, the second peak of curve D6 is estimated to be on the plateau shown. In FIG. 13, the second peak of the curve DIP10 is not clearly shown. The complete plots or curves of FIGS. 6–14 are not shown since the complete curves are not necessary to determine the second peaks. Selecting the second peaks is based on one's experience and knowledge of the system. Some of the second peak shutter speeds of the table of FIG. 4 were taken from the curves of FIGS. 6–14.

I claim:

1. A method of inspecting solder joints of a circuit card assembly with a laser inspection system comprising a laser capable of being operated at a suitable power in watts to produce a laser beam for a selectable duration for application to a solder joint of a circuit card assembly and a detector system for detecting infra red emission from the heated solder joint to determine the solder joint integrity, said method comprising the steps of:

for a given type of circuit card assembly, selecting a laser beam time duration for a laser to be operated at a given power level which is effective to result in the detection of a peak number of defective solder joints of the same type in said given type of circuit card assembly, said peak number of defective solder joints being the second peak relative to a given base determined from prior testing of said given type of solder joints in said given type of circuit card assembly at a plurality of different laser beam time durations, operating said laser at said given power level to apply a laser beam to a solder joint of said given type in said given type of circuit card assembly for the selected time duration for heating said solder joint, and detecting infra red emission from said solder joint resulting from said laser beam heating step to determine the integrity of said solder joint.

2. The method of claim 1, wherein:
said laser is operated at a power level of at least 15 watts.

3. The method of claim 1, wherein said prior testing is carried out by the steps comprising:

operating said laser at said given power level to produce a laser beam for different time durations and applying said laser beam for each of said different time durations to a plurality of a given type of said solder joints in a plurality of said given type of circuit card assemblies, detecting infra red emissions from each solder joint and resulting from said laser beam applied to each solder joint, the infra red emissions at a given time of the cooling curve of said solder joints identifying a normal distribution for each of said laser beam durations, determining the variance and an average value from each of said distributions to determine upper and lower limits on each side of the average, determining the number of events that fall outside of said upper and lower units for each laser beam duration wherein each of said events determined represents a defective solder joint, from each event determined from each of said laser beam durations, forming a function representative of the number of said events determined, and from said function, determining said second peak of defective solder joints.

4. The method of claim 3, wherein:
said laser is operated at a power level of at least 15 watts.

5. The method of claim 3, wherein:
said laser is operated to produce a laser beam for a number of different time durations greater than two and said laser beam produced for said number of different time durations is applied to each of said given type of said solder joints in said plurality of said given type of circuit card assemblies.

6. The method of claim 5, wherein:
each of a plurality of said different time durations is greater than sixty milliseconds.

7. The method of claim 6, wherein:
said given type of said solder joints comprises a component lead.

8. The method of claim 5, wherein:
said given type of said solder joints comprises a component lead.

9. The method of claim 3, wherein:
said given type of said solder joints comprises a component lead.

10. A method of producing a function for use for determining the integrity of solder joints in circuit card assemblies, comprising the steps of:

operating a laser at a given power level to produce a laser beam for different time durations and applying said laser beam for each of said different time durations to a plurality of a given type of solder joints in a plurality of a given type of circuit card assemblies, detecting infra red emissions from each solder joint and resulting from said laser beam applied to each solder joint, the infra red emissions at a given time of the cooling curve of said solder joints identifying a normal distribution for each of said laser beam durations, determining the variance and the average value from each of said distributions to determine upper and lower limits on each side of the average, determining the number of events that fall outside of said upper and lower units for each laser beam duration wherein each of said events determined represents a defective solder joint, from each event determined from each of said laser beam durations, forming a function representative of the number of said events determined, and from said function, determining the second peak from a given base.

11. The method of claim 10, wherein:
said laser is operated at a power level of at least 15 watts.

12. The method of claim 10, wherein:
said laser is operated to produce a laser beam for a number of different time durations greater than two and said laser beam produced for said number of different time durations is applied to each of said given type of said solder joints in said plurality of said given type of circuit card assemblies.

13. The method of claim 12, wherein:
each of a plurality of said different time durations is greater than sixty milliseconds.

14. The method of claim 13, wherein:
said given type of said solder joints comprises a component lead.

15. The method of claim 12, wherein:
said given type of said solder joints comprises a component lead.

16. The method of claim 10, wherein:
said given type of said solder joints comprises a component lead.

* * * * *